United States Patent [19]
Thorne et al.

[11] Patent Number: 5,656,031
[45] Date of Patent: Aug. 12, 1997

[54] MEDICAL SYRINGE AND SELF RETRACTING NEEDLE APPARATUS

[75] Inventors: Gale H. Thorne; David L. Thorne, both of Bountiful, Utah

[73] Assignee: Specialized Health Products, Inc., Bountiful, Utah

[21] Appl. No.: 595,802

[22] Filed: Feb. 2, 1996

Related U.S. Application Data

[63] Continuation-in-part of Ser. No. 565,881, Dec. 1, 1995, which is a continuation-in-part of Ser. No. 455,514, May 31, 1995, Pat. No. 5,549,708, which is a continuation of Ser. No. 370,728, Jan. 10, 1995, Pat. No. 5,480,385, which is a continuation-in-part of Ser. No. 436,976, May 8, 1995, Pat. No. 5,487,734, which is a continuation-in-part of Ser. No. 484,533, Jun. 7, 1995, Pat. No. 5,542,927.

[51] Int. Cl.$^6$ ............................................................. A61M 5/00
[52] U.S. Cl. ............................... 604/110; 604/195; 604/263
[58] Field of Search ............................................. 604/110, 187, 604/192, 195, 198, 263

[56] References Cited

U.S. PATENT DOCUMENTS

| | | | |
|---|---|---|---|
| 3,587,575 | 6/1971 | Lichenstein | 128/128 |
| 4,676,783 | 6/1987 | Jagger | 604/171 |
| 4,813,936 | 3/1989 | Schroeder | 604/195 |
| 4,850,374 | 7/1989 | Diaz-Ramos | 128/763 |
| 4,892,525 | 1/1990 | Hermann, Jr. | 604/263 |
| 4,909,794 | 3/1990 | Haber | 604/195 |
| 4,936,830 | 6/1990 | Verlier | 604/110 |
| 4,946,446 | 8/1990 | Vadher | 604/198 |
| 4,955,870 | 9/1990 | Ridderheim | 604/195 |
| 4,966,593 | 10/1990 | Lennox | 604/198 |
| 4,978,340 | 12/1990 | Terrill | 604/195 |
| 4,985,021 | 1/1991 | Straw | 604/198 |
| 4,986,816 | 1/1991 | Steiner | 604/192 |
| 4,988,339 | 1/1991 | Vadher | 604/197 |
| 4,994,034 | 2/1991 | Botich | 604/110 |
| 4,995,870 | 2/1991 | Baskas | 604/110 |
| 5,092,853 | 3/1992 | Couvertier | 604/195 |
| 5,098,402 | 3/1992 | Davis | 604/195 |
| 5,114,404 | 5/1992 | Paxton | 604/110 |
| 5,147,303 | 9/1992 | Martin | 604/110 |
| 5,180,370 | 1/1993 | Gillespie | 604/110 |
| 5,188,599 | 2/1993 | Botich | 604/110 |
| 5,193,552 | 3/1993 | Columbus et al. | 128/760 |
| 5,195,983 | 3/1993 | Boese | 604/192 |
| 5,195,985 | 3/1993 | Hall | 604/195 |
| 5,205,823 | 4/1993 | Zdeb | 604/110 |
| 5,205,824 | 4/1993 | Mazur | 604/110 |

(List continued on next page.)

OTHER PUBLICATIONS

Patricia Seremet, "Small Tolland Company Takes Jab at Safety Needle Market," *The Hartford Courant*, Sep. 13, 1995, pp: F1 and F3.

*Primary Examiner*—John D. Yasko
*Attorney, Agent, or Firm*—Gale H. Thorne

[57] ABSTRACT

Method and apparatus associated with safe retraction of medical needles after use. Embodiments are disclosed for combinations comprising medical syringes and self-retracting needle systems. An energy-storing, needle-retracting mechanism comprises an elastic tubing which also is taught perform a plurality of functions comprising the storing of force by which a medical needle is retracted, slidable seals, normally closed valves and dynamic volume control by which fluid regurgitation upon needle retraction is voided. Selective, constrictive control of the internal volume of the tubing when stretched effectively inhibits regurgitant flow from the needle as the tubing relaxes while retracting the needle. In all embodiments, needle retraction is initiated by forces applied in a direction transverse to the long axis of the needle using but a single hand. The syringe may be used in a plurality of modes such as a standard syringe or as a pre-filled syringe. Methods for making and assembling the combination are also disclosed. Invention manufacture requires only a minimal number and complexity of parts such that a projected manufacturing cost is potentially low enough to permit the apparatus to be cost competitive with contemporary combinations of hypodermic syringes and non-self retracting needle systems.

31 Claims, 11 Drawing Sheets

U.S. PATENT DOCUMENTS

| | | | |
|---|---|---|---|
| 5,209,739 | 5/1993 | Talslay | 604/195 |
| 5,215,533 | 6/1993 | Robb | 604/195 |
| 5,246,428 | 9/1993 | Falknor | 604/198 |
| 5,254,099 | 10/1993 | Kuracina | 604/198 |
| 5,256,153 | 10/1993 | Hake | 604/198 |
| 5,267,976 | 12/1993 | Guerineau | 604/198 |
| 5,320,606 | 6/1994 | Jore | 604/110 |
| 5,356,392 | 10/1994 | Firth et al. | 604/198 |
| 5,374,250 | 12/1994 | Dixon | 604/110 |

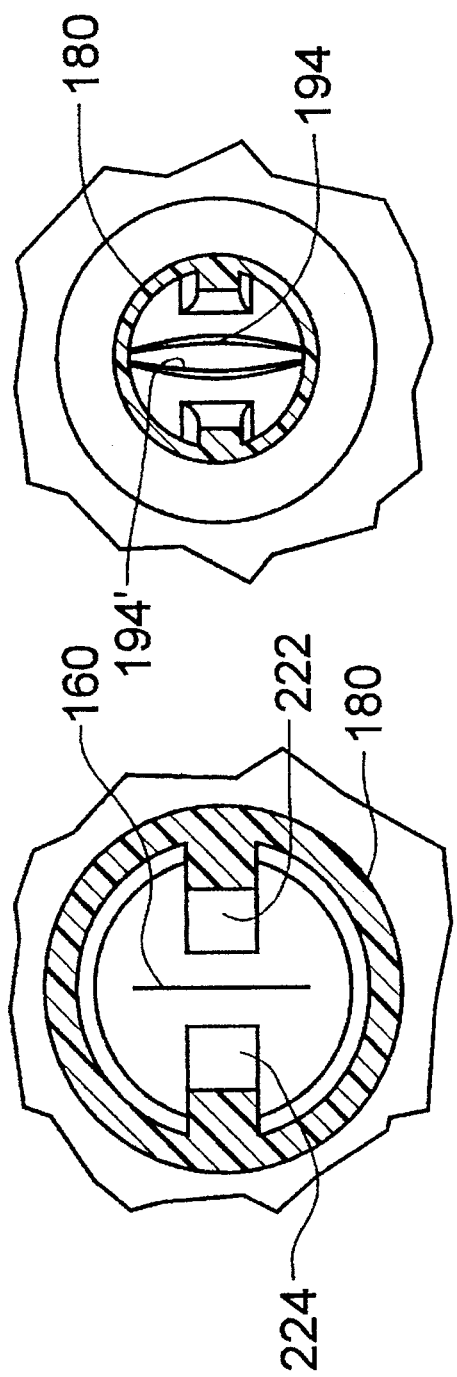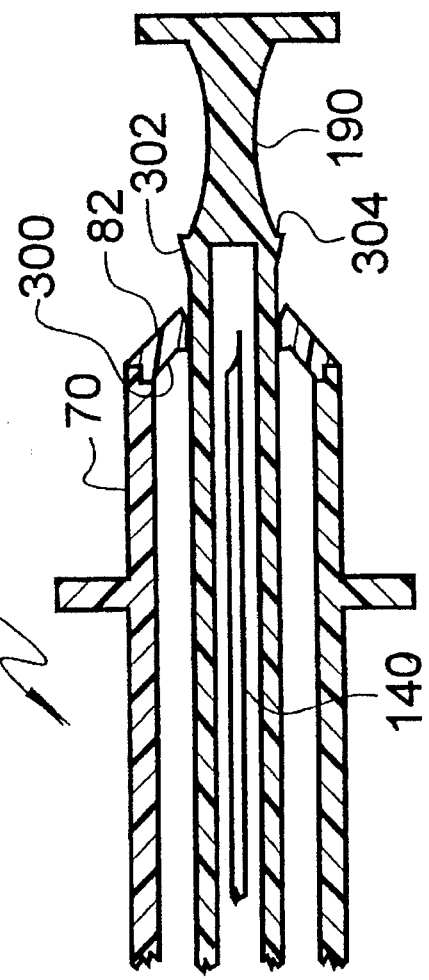

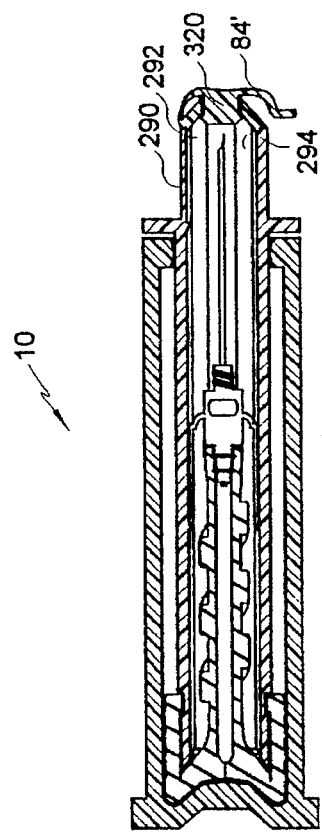
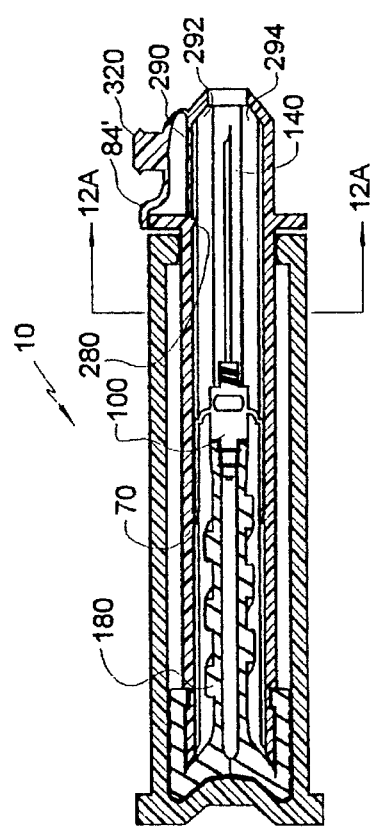

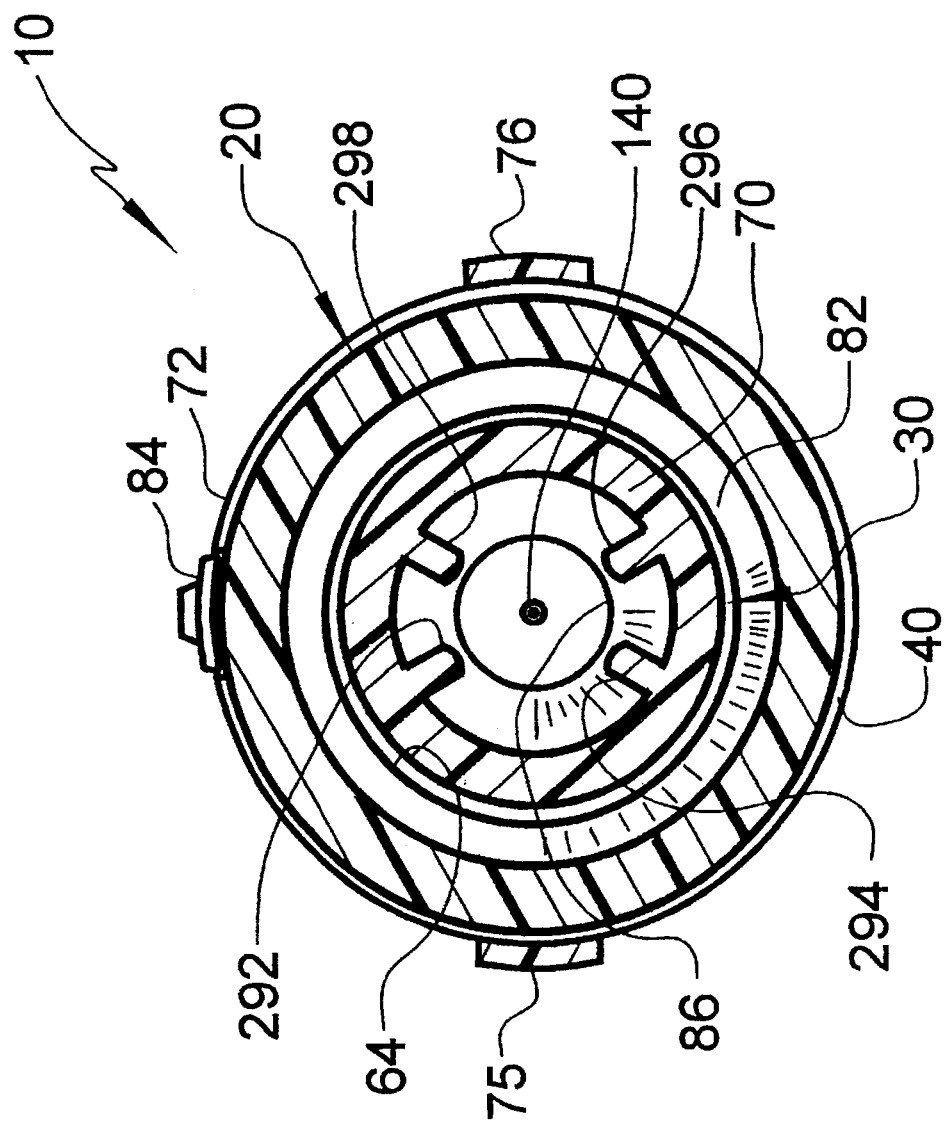

MEDICAL SYRINGE AND SELF RETRACTING NEEDLE APPARATUS

CONTINUATION

This application for patent is a continuation-in-part of U.S. patent application Ser. No. 08/565,881, filed Dec. 1, 1995, which is a continuation-in-part of U.S. patent application Ser. No. 08/455,514 filed May 31, 1995 now U.S. Pat. No. 5,549,708, which is a continuation of U.S. patent application Ser. No. 08/370,728 filed Jan. 10, 1995, now allowed as U.S. Pat. No. 5,480,385, and of U.S. patent application Ser. No. 08/436,976 filed May 8, 1995, now U.S. Pat. No. 5,487,734 and U.S. patent application Ser. No. 08/484,533 filed Jun. 7, 1995, now U.S. Pat. No. 5,542,927 and are continuations-in-part of U.S. Pat. No. 5,480,385.

FIELD OF INVENTION

This invention relates generally to medical syringes and associated medical needle apparatus and methods and particularly to medical syringes comprising integral retracting mechanisms for medical needles for retracting a needle from an extended position at which the needle is used to a retracted position where the needle is fully withdrawn and encased within a housing for safe disposal. Further, the invention is related to medical products which may only be selectively used either once or multiple times, but which are restricted from continued use thereafter to void cross contamination from one patient to another and to those medical products which have sterile parts inherently protected from contamination without need of additional protective packaging apparatus.

PRIOR ART

Problems associated with inadvertent needle sticks are well known in the art of blood withdrawal, percutaneous medication injection, catheter emplacement and other medical procedures involving uses of medical needles. Ever increasing attention is being paid to needle stick problems due to the contemporary likelihood of being exposed to AIDS and Hepatitis.

Commonly, procedures involving removing a needle from a patient require a technician to use one hand to place pressure at the wound site where a needle is being withdrawn while removing the needle apparatus with the other hand. It is common practice for a tending technician to give higher priority to care for the wound than is given to disposal of a needle. Such priority either requires convenience of an available sharps container within ready reach or another means for safe disposal without leaving the patient's side. Providing adequate care is often compounded by patient condition and mental state (e.g. in burn units and psychiatric wards). Under such conditions, it is often difficult, if not impossible, to take appropriate procedures to properly dispose of a used, exposed needle while caring for a patient.

Widespread knowledge and history associated with needle care and disposal problems have resulted in conception and disclosure of a large number of devices each of which represents an attempt to provide not only a solution to the problem of needle sticks, but also a device which is commercially viable (i.e. cost and price competitive with currently used non-self retracting devices). Though some devices describe application in the area of blood withdrawal (see U.S. Pat. No. 4,850,374 (Nydia Diaz-ramos) and U.S. Pat. No. 5,195,985 (Hall)), most contemporary related art is directed toward syringes and like devices. Broadly, related art may be classified into two categories, devices which operate manually and devices which comprise self-contained needle retraction.

Examples of manually operated medical needle devices are provided in U.S. Pat. No. 4,676,783 (Jagger et al.), U.S. Pat. No. 4,83,936 (Schroeder), U.S. Pat. No. 4,909,794 (Haber), U.S. Pat. No. 4,978,340 (Terrill et al.), U.S. Pat. No. 4,995,870 (Baskas), U.S. Pat. No. 5,098,402 (Davis), U.S. Pat. No. 5,180,370 (Gellespie), U.S. Pat. No. 5,188,599 (Botich et al.), U.S. Pat. No. 5,195,985 (Hall), U.S. Pat. No. 5,205,823 (Zdeb), U.S. Pat. No. 5,205,824 (Mazur), U.S. Pat. No. 5,215,533 (Robb), and U.S. Pat. No. 5,256,153 (Hake). Manual withdrawal is generally a two-handed procedure, making wound care a secondary step or requiring an added medical technician.

Examples of self-retracting devices are found in U.S. Pat. No. 4,946,446 (Vadher), U.S. Pat. No. 4,955,870 (Ridderheim et al.), U.S. Pat. No. 4,966,593 (Lennox), U.S. Pat. No. 4,988,339 (Vadher), U.S. Pat. No. 4,994,034 (Botich et al.), U.S. Pat. No. 5,114,404 (Paxton et al.), U.S. Pat. No. 5,147,303 (Martin), U.S. Pat. No. 5,092,853 (Couvertier), U.S. Pat. No. 5,246,428 (Falknor), U.S. Pat. No. 5,254,099 (Karacina), U.S. Pat. No. 5,267,976 (Guerineau et al.), U.S. Pat. No. 5,209,739 (Talalay) and U.S. Pat. No. 5,320,606 (Jore). Guerineau et al. discloses self-retraction resulting from a vacuum force while others disclosed above generally disclose self-retraction resulting from release of a cocked or biased spring.

Of particular interest is a single use hypodermic safety syringe disclosed in U.S. Pat. No. 5,320,606 (Jore). Jore teaches use of an elastic tube in a hypodermic syringe which is used both as a pathway for fluid and as a means of retracting a medical needle which is taught to be attached to the syringe after the elastic tube is stretched. The hypodermic syringe taught by Jore comprises a hollow syringe barrel, open on one end and closed on the other, and a hollow plunger assembly. A similar hypodermic syringe having a hollow syringe barrel and a hollow plunger assembly is also taught in U.S. Pat. No. 4,936,830 (Verlier) and U.S. Pat. No. 3,587,575 (Lichtenstein) issued Jun. 28, 1971.

Art cited by Jore is U.S. Pat. No. 5,209,739 (Talalay) which discloses a hypodermic needle assembly an elastomeric tube held in a stressed state such that the tube retracts an attached cannula with sufficient force to pull the cannula from a patient. Embodiments for use as syringe and blood draw devices are disclosed.

Generally, other than acceptance of the type of operation offered by such devices, commercial viability is dependent upon manufacturing cost. Purchase decisions in the area in which these devices are used are very cost sensitive. If gains in either improvement in safety or in labor savings are not found to make a device sufficiently competitive with contemporary competitive items, those devices are usually not found to be commercially viable. Motivation for providing a cost competitive self-retracting needle apparatus coupled with improved safety of use of the apparatus resulted in conception of the instant inventions disclosed herein.

BRIEF SUMMARY AND OBJECTS OF THE INVENTION

In brief summary, the novel inventions disclosed herein dramatically diminish known major problems resulting from injury-related needle sticks which occur when needle tips are bared as syringe borne medical needles are withdrawn from a patient at the end of a needle insertion procedure. In preferred embodiments, operation of the invention involves elongating a medical needle apparatus from a protective housing and providing access to a medical needle which is also enclosed and protected by a needle cover prior to use. In all embodiments, the act of elongating the apparatus energizes a force storing memory element and cocks a releasable latch. Generally, the needle is made available for a medical procedure by physically separating a needle cover from the rest of the apparatus immediately prior to use. Once the cover is removed, the needle is used in a medical procedure (e.g. for acquiring a blood sample or for medical fluid injection).

In a preferred embodiment, when the medical procedure is complete, a simple depression of a portion of the housing, preferably by squeezing the housing by the thumb and forefinger of one hand, retracts the needle safely into the housing. It is important to note that the needle can be removed directly from a patient and safely encased in the housing by a simple action of a single hand of an attending technician, leaving the technician's other hand free for other concurrent medical procedures, such as care of the wound site from which the needle is retracted. After retraction, the needle is fully enclosed and contained, permitting the needle apparatus to be laid aside without fear of an inadvertent needle stick while full attentive care is provided to the patient.

Generally, these novel inventions are for a self-retracting medical syringe and needle apparatus which are employed in transporting, using and retracting a medical needle into safe containment Within a housing after use. In all cases, the apparatus comprises the housing into which the medical needle is retracted at the end of a medical procedure. In a preferred embodiment, in addition to the housing, the apparatus comprises a syringe which is prefilled for unit dose applications, a needle cover, a medical needle assembly, a needle support catch and a linear motion energy storage member.

In another preferred embodiment, the apparatus permits attachment of a standard medical needle to be attached, such as by a luer-lock fitting immediately before the apparatus is used in a medical procedure. In two specific embodiments, the syringe employs a normally-closed valve which is opened when the needle apparatus or needle is extended for use. The valve is likewise closed when the needle is retracted. The syringe comprises geometry which permits absolutely safe recapping of the needle and subsequent reextension to permit a prefilled syringe to be used for multiple injections without requiring a full dose to be administered before retracting the needle to safe containment. Even so, the needle is safely contained by retraction into the housing after each injection.

In a preferred method, the apparatus is triggered by a technician causing the needle to be retracted directly from a patient by the apparatus and, in a continuing motion, to be deposited into the housing. When desired, the needle is safely and sterilely recapped while it resides within the housing wherefrom it is reextended for subsequent use.

The syringe is characterized by an elongated barrel which is closed on one end and a hollow plunger assembly which comprises the needle housing and houses the needle extension and retraction apparatus. The closed end of the barrel comprises a generally convex inner surface to facilitate expulsion of undesirable gases as is standard practice when preparing contents of a syringe immediately prior to use. In a preferred embodiment, the closed end also comprises a closable and sealable access port through which the barrel may be prefilled.

The plunger comprises a seal which is disposed between the exterior of the plunger and interior of the elongated barrel and provides a slidable seal to permit introduction into and expulsion of fluids from a fluid containment space between the barrel and plunger. In a preferred prefilled syringe embodiment, exit from and entrance of fluid into the space is blocked by a valve disposed between the space and a pathway to the needle. It is preferred that the pathway be an elastic tube having a normally-closed slit valve blocking flow from the space into the pathway. It is also preferred that the slit valve be opened when the tube is stretched when the needle is extended for use.

The needle housing is further characterized by an elongated, generally cylindrical shape having an opening at one end wherethrough the medical needle passes. To prepare the apparatus for use, the apparatus is elongated to an extended state by moving the one end apart from an opposing end of the housing. In this manner, the medical needle which is most closely associated with the one end is also moved apart from the opposing end. To assure that the medical needle is affixed in a stable condition relative to the housing, the housing comprises a catch for a latch which secures the apparatus in the extended state.

When the apparatus is in the extended state, a medical needle assembly associated with the medical needle is cocked, ready to be released to thereby retract the medical needle into the housing. A predetermined portion of the housing is dedicated to communicating a releasing action upon a trigger action which disengages the latch from the catch, thereby causing the medical needle to be retracted into the housing. The dedicated housing portion is preferably a deformable section of the housing which, when deformed, communicates with the releasible latch. In a preferred embodiment, an easily removed shield is used to cover the dedicated, communicating portion of the housing to prevent inadvertent latch release and subsequent premature retraction of the needle from the patient.

Before use, at least a portion of the needle cover generally extends outwardly from the one end of the housing. The needle cover and housing, in combination, commonly provide a measure of protection for maintaining sharpness and sterility of the medical needle. Further, in a preferred embodiment, the cover provides a handle which is used in elongating the apparatus.

In addition to the medical needle, the medical needle assembly comprises a secure attachment to the medical needle, the releasible latch which is affixed to the needle support catch when the apparatus is elongated for use, the latch release and a connecting hub which is integral with the needle attachment and a hub which is used to affix the needle and attachment to a linear motion energy storage member. The medical needle assembly is substantially disposed within the housing and cover for transport and storage prior to use. When properly used, the medical needle is bared for use in a medical procedure subsequent to elongating the apparatus.

In a preferred embodiment, the needle support catch is an integral part of the housing. The needle support catch is disposed to engage the latch and thereby securely affix the needle when the apparatus is elongated.

The linear motion energy storage member may be a spring, a piston which draws a vacuum in a chamber as the apparatus is extended or any component which stores retracting energy as the apparatus is elongated. However, the preferred storage member is an elastic tube which not only stores potential energy for needle retraction as the apparatus is elongated, but also provides a pathway for fluid which is passed through the needle during the medical procedure and a means for voiding regurgitant flow from a retracting needle.

Preferred materials for the elastic tube are silicone rubber and medical grade latex, although other tubing materials may be used within the scope of the invention. It should be noted that the elastic tubing is preferably in a rest or unstretched state while the apparatus is being transported or stored prior to use. The elastic tube is only stretched (stressed) when the apparatus is elongated for use.

As the needle may be directly retracted from a patient, it is preferred that fluid flow from the needle be kept to an absolute minimum during retraction. Due, at least in part, to tubing expansion about a hub when the elastic tube is stretched, most often an extended tube defines an internal volume which is larger than the internal volume same tube when unstretched. Generally that internal volume difference is a function of the difference in diameter of the internal diameter of the unstretched tube and the external diameter of a hub which connects and secures one end of the elastic tube to the apparatus. For this reason, it is preferred to utilize a hub having substantially the same external diameter as the internal diameter of the tube when unstretched.

However, even when utilizing hubs having such restricted diameters, a small amount of regurgitant flow is still possible when the tube is released from a stretched state to constrict into a relaxed state. It has been found through experimentation that the volume of the tubing when stretched must be physically constricted to a volume which is less than that of the tubing when unstretched to assure that no regurgitant flow can occur under such conditions, Several mechanisms for so constricting the tubing have been successfully tested.

A preferred tube constricting mechanism comprises a helical wrap disposed about the elastic tube. As the tube is stretched, the helical wrap reacts to partially choke the tube to reduce the inner volume of the stretched tube to be less than that of the relaxed tube. This mechanism eradicates the causes of liquid regurgitation as the medical needle is retracted into the housing.

In general, use of the apparatus comprises the steps of elongating the apparatus thereby positioning a medical needle relative to parts moved away from the needle during apparatus elongation, affixing the needle thereat, storing energy in a linear energy storage member and cocking a trigger for later release; exposing the needle; performing a medical procedure on a patient and, while the needle is still resident in the patient, accessing a portion of the housing in communication with the trigger; actuating the trigger by action of a single hand, in a direction transverse to the long axis of the needle, to retract the needle directly from the patient into an enclosed housing for safe disposal within the apparatus.

It is noted that, except for needles which are integrally connected to injection molded parts and an elastic tube, all parts are injection molded. In a preferred embodiment, the functions of providing a seal between the barrel and plunger, an interface to the convex inner surface of the barrel, the normally-closed valve and the elastic tube be formed as one integral part.

Accordingly, it is a primary object to provide a novel and improved combination comprising a medical syringe and extendable and self-retracting medical needle apparatus.

It is a chief object to provide a combination which protects physical integrity and sterility of internal parts of the combination until use and which automatically fully retracts the needle into the housing after use.

It is an important object to provide a syringe barrel as part of the medical syringe which comprises an elongated hollow cylindrical portion having a fluid contacting surface interior to the barrel part.

It is a fundamental object to provide a plunger assembly which comprises an exterior seal and associated surface which interfaces with the syringe barrel to define a fluid containment space in cooperation with the fluid contacting surface of the syringe barrel such that repositioning the barrel relative to the plunger assembly varies the volume of the space, the plunger assembly also comprising a hollow elongated hollow cylinder which is sized to slide within, without contacting, the hollow cylindrical portion of the syringe barrel.

It is a key object to provide the plunger assembly having the elongated hollow chamber, a portion of which is disposed within said hollow cylindrical portion of the syringe barrel and a portion of which comprises an exterior surface segment which is accessible to a user, said segment further comprising a depressible section.

It is another key object to provide a slidable seal disposed between the barrel and plunger assembly to aid in containing fluid within the space.

It is an object to provide, disposed within the hollow cylinder of the plunger, a catch for a latch, the catch being disposed to releasibly secure the latch in physical communication with the depressible section such that depressing the depressible section releases the latch from the catch.

It is another fundamental object to provide the extendable and self-retracting medical needle apparatus comprising an elastic tube which when extended as the medical needle apparatus is extended provides both a pathway for medical fluids between the medical needle apparatus and the space and a retractive force whereby the needle is retracted when the latch is freed from the catch.

It is still another fundamental object to provide a medical needle hub which affixes to a proximal end of the elastic tube, a releasible union which attaches to a member used to extend the medical needle apparatus to a position at which the medical needle is used and a releasible latch for the catch, the latch being releasible by depressing the depressible section, the depressing being in a direction transverse to the long axis of the medical needle and the release of the latch from the catch being independent of the position of the syringe barrel and plunger assembly.

Further, it is an object to provide a normally closed valve which is disposed between the space and the fluid pathway and which is opened by extending the elastic tube such that a liquid is fully contained within the space until the syringe is readied for use.

It is another object to provide a normally closed valve which is a slit valve.

It is an object to provide a single part which comprises the elements of the slit valve and elastic tube.

It is an important object to provide a single part which comprises the slit valve, the elastic tube and slidable seal.

It is an object to provide a barrel having an closable orifice through which the space is filled with a medical fluid to produce a prefilled syringe.

It is an object to provide a stopper to close the orifice after the space is filled such that fluid can only exit through the medical needle apparatus.

It is an object to provide a medical needle securely affixed to the medical needle hub.

It is an object to a medical needle hub which comprises a luer-lock fitting whereby a medical needle is affixed after the medical needle hub is extended.

It is an object to provide a means of extending by pulling the medical needle apparatus, the extending means being removably affixed to the medical needle hub.

It is an object to provide an extending means which is also a needle cover which provides a sterile barrier for a medical needle during transport and immediately prior to use after extending the medical needle apparatus.

It is an object to provide guides internally disposed in the plunger which permit a needle cover to be safely replaced over a retracted medical needle without injury to a user or further contamination of the medical needle.

It is an object to provide a seizing catch inside the plunger to lock a complementary latch associated with the medical needle apparatus when the medical needle apparatus is forced into the plunger sufficiently far to buckle the elastic tube.

It is an object to provide at least one handle disposed upon the plunger by which the barrel and plunger are moved one relative to the other by a single hand.

It is an object to provide, as part of the combination, medical liquid stored and transported within the space.

It is an object to provide on an end of the barrel distal from the medical needle apparatus an internal surface which is convex in the direction of the medical needle apparatus having a centrally disposed apex.

It is an object to provide the apex juxtaposed the fluid pathway.

It is an object to provide a complementary surface to the internal surface, the complementary surface being a part of parts forming the fluid pathway and forming a geometry which permits facile purging of gas from the space through the fluid pathway.

It is an object to provide a removable shield disposed about the depressible section which obstructs inadvertent depression by a user and therefore preliminary retraction of the medical needle apparatus and yet is facilely removed to permit access to the depressible section for easily triggering retraction of the medical needle apparatus.

It is another primary object to provide a method for using a prefilled syringe comprising an important step of applying a force to trigger needle retraction which is transverse to the axis of the medical needle.

It is an object to provide a method for releasing the medical needle apparatus for subsequent retraction into a protective housing independent of position of the barrel relative to the plunger.

It is an object to provide a method for extending the medical needle apparatus from the plunger using a needle cover as a puller.

It is a very important object to provide a method for safely replacing a cover over a medical needle without further contaminating the needle.

It is an object to provide a method for seizing a cover when forcefully and deeply inserted into the plunger to negate subsequent use of the medical syringe.

It is another key object to provide a method whereby a needleless syringe and medical needle apparatus combination is affixed to a medical needle after the medical needle apparatus is extended.

It is another fundamental object to provide a syringe and medical needle apparatus combination, the syringe being prefilled prior to transport to a user and the medical needle assembly being extendable for use of the medical needle use and being retractable for safe storage of the needle after use.

It is another fundamental object that the combination comprise at least one seal which effectively contains a medical solution in an effective state prior to administration of the solution.

It is a very important object that the combination be made with as few injection molded parts as possible.

It is a significant object to provide a manufacturing method for assembly of the device which is compatible with automatic assembly equipment.

It is an object to provide a force storing memory element which stores energy as the apparatus is extended and which provides needle retracting force upon release of the needle assembly.

It is a meaningful object to provide a memory element which comprises an enclosed fluid flow pathway for withdrawn blood.

It is an object to nullify forces within the apparatus which cause regurgitant flow when the needle is retracted.

These and other objects and features of the present invention will be apparent from the detailed description taken with reference to accompanying drawings.

BRIEF DESCRIPTION OF THE DRAWINGS

FIG. 4 is a transverse cross section of an elastic tube and slit valve seen in cross section in FIGS. 2 and 3.

FIG. 5 is a transverse cross section of the elastic tube and slit valve seen in FIG. 4 with the elastic tube elongated to open the slit valve.

FIG. 12 is a cross section of a lateral elevation similar to the combination seen in FIG. 2, but with a plug disposed upon a shield located above and protecting a depressible, distortable section of the plunger section.

FIG. 12A is a cross section taken along lines 12A—12A in FIG. 12.

FIG. 13 is a cross section of the lateral elevation of FIG. 12 with the shield rotated to affix the plug into the plunger section.

FIG. 14 is a cross section of a ventral portion of a combination, similar to the combination seen in FIG. 1, showing latches and catches used to limit use of the combination by forcing the needle cover deeply into the plunger part.

DETAILED DESCRIPTION OF THE ILLUSTRATED EMBODIMENTS

In this description, unless a specific object is referenced, the term proximal is used to indicate the segment of a device normally closest to the patient when it is being used. In like manner, the term distal refers to the other (away from the patient) end. Reference is now made to the embodiments illustrated in FIGS. 1–18 wherein like numerals are used to designate like parts throughout. In some cases, parts having similar form and function to parts earlier cited are enumerated with prime numerals of the earlier cited parts.

Figure 1:
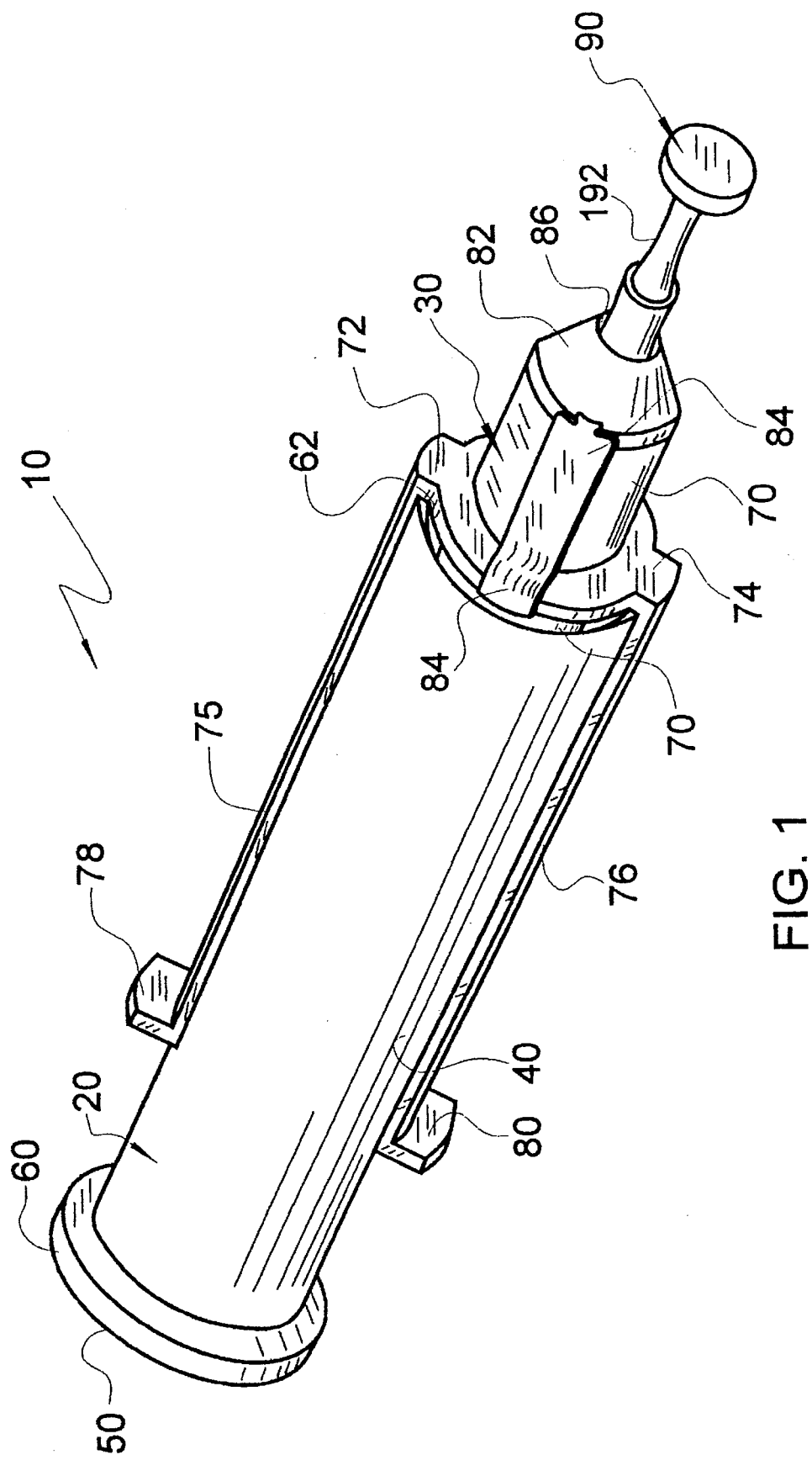
FIG. 1 is a perspective of a combination syringe and medical needle apparatus.

Reference is now made to FIG. 1 wherein an embodiment according to the invention of a combination syringe/medical needle apparatus 10 is seen. As seen in FIG. 1, combination 10 comprises a syringe barrel 20 and a plunger part 30.

Barrel 20 comprises a hollow elongated tube member 40 and a distal end 50 which is transversely disposed to member 40. Preferably, a section 60 at distal end 50 has a generally larger radius of curvature than the curvature of member 40 to permit barrel 20 to be facilely gripped and moved relative to part 30. Proximally, an end 62 provides an entry and exit orifice 64 for plunger part 30.

Plunger part 30 also comprises a hollow elongated tube member 70 which is sized to fit-without-touching-inside member 40. Extending radially outward from member 70 is a securely affixed appendage 72 which is disposed to be in near proximity, but not to touch end 62. Preferably, appendage 72 comprises a proximal face 74 which is generally large enough to be gripped with a fore finger and an index finger for use in single handed syringe manipulation.

Extending distally from appendage 72 and juxtaposed member 40 are a pair of opposing members 75 and 76 which end abruptly in outwardly distending handles 78 and 80, respectively. The length of members 75 and 76 are dependent upon the length of barrel 20 and are adjusted to provide facile single handed syringe manipulation. Such adjustments are well known in the art of syringe design. Outward extension of handles 78 and 80 should be sufficient to provide digitary control using index and middle fingers.

Proximally plunger part 30 terminates in a hollow frustoconical nose cone 82 to which a shield 84 is attached. The purpose and function of shield 84 is disclosed in detail hereafter. Nose cone 82 comprises an axially disposed orifice 86 through which a medical apparatus puller 90 operates to extend a medical needle apparatus 100, an example of which is seen in cross section in FIG. 2.

Figure 2:
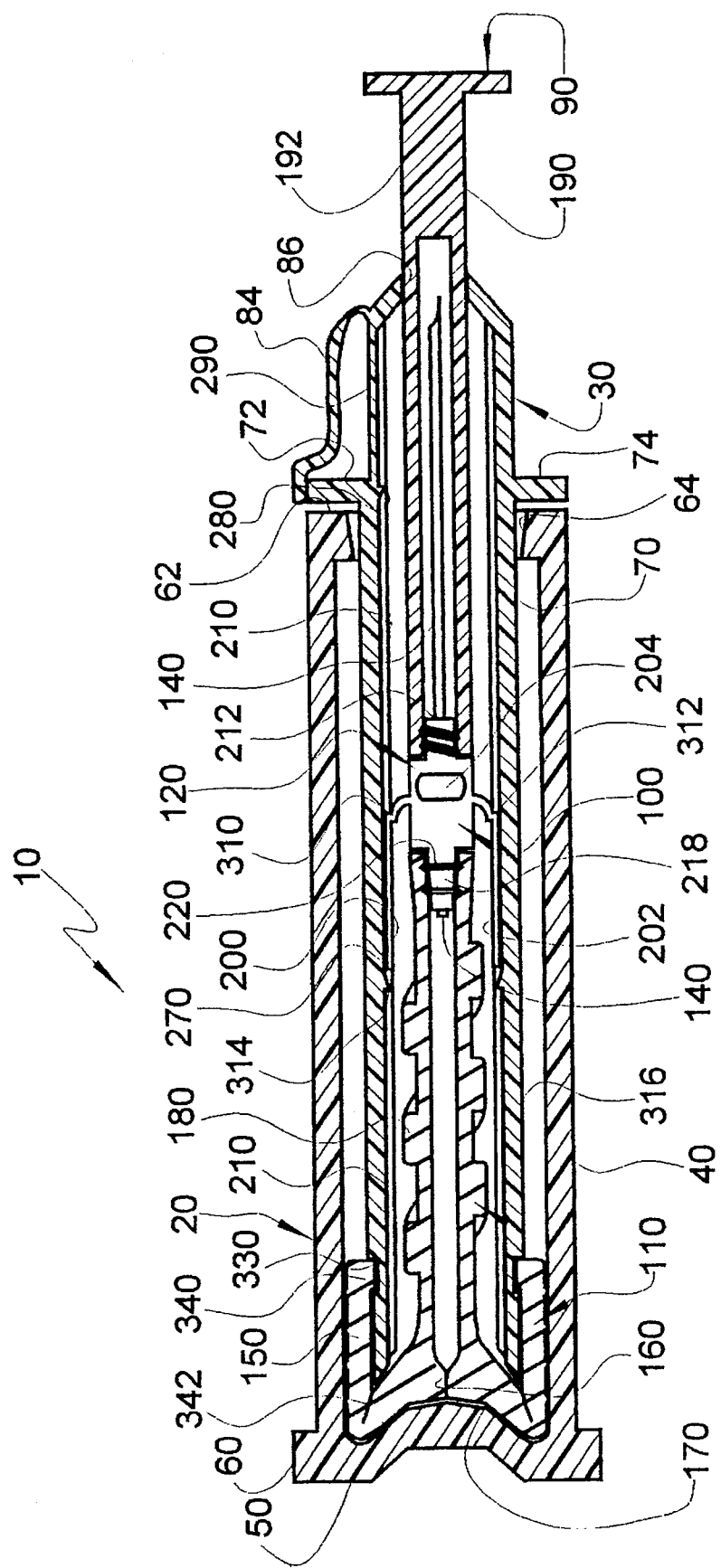
FIG. 2 is a cross section of a lateral elevation of the combination seen in FIG. 1.

Referring to FIG. 2, medical needle apparatus 100 is seen to comprise a pliant and stretchable elastic component 110, a hub element 120 and a hollow medical needle 140. While component 110 may be made as a number of separate parts, it is presently preferred that component 110 comprise integrally formed and attached parts which functionally perform as a seal 150, a normally closed valve 160, an interfacing surface 170 to a ventral surface of a posterior portion of barrel 20 and an elastic tube 180. In the embodiment of FIGS. 1 and 2, valve 160 is a slit valve.

As is common with standard contemporary disposable syringes, member 40 comprises an opening 64, comprising a frustoconical shape which is conducive to passage of seal 150 in a direction into member 40, but unfavorable to release of seal 150 from member 40.

In this case, puller 90 is a needle cover 190 which physically and asceptically protects needle 140. A portion 92 of cover 190 is exteriorly accessible through orifice 86.

Figure 3:
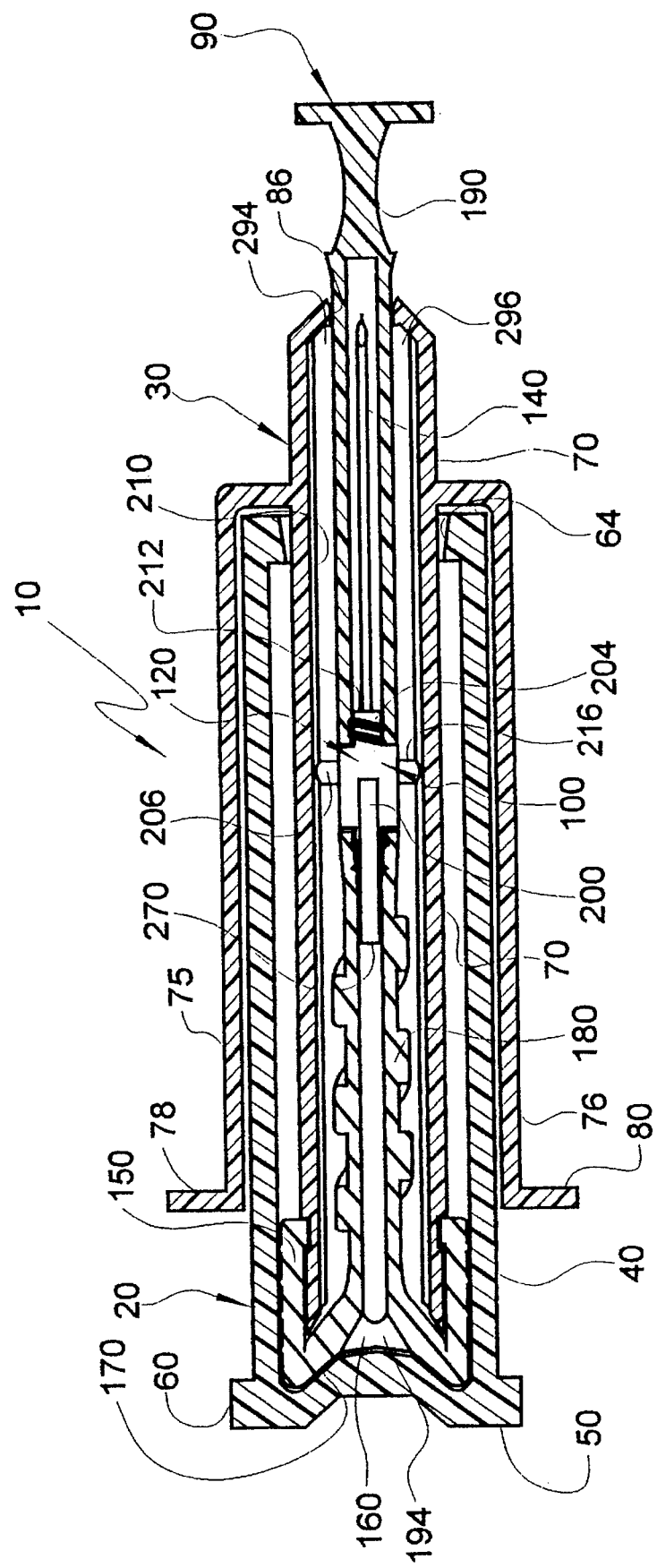
FIG. 3 is a cross section of a lateral elevation or the combination seen in FIG. 1 but rotated 90° relative to that seen in FIG. 2.

In FIG. 3, device 10 is seen in cross section rotated 90° about the long axis of needle 140. This rotation gives visibility to opposing members 75 and 76. The rotation also gives visibility to a planar face 194 of slit valve 160.

Referring now to FIGS. 2 and 3 in combination, hub element 120 is seen to comprise a superior wing part 200, an inferior wing part 202 and a pair of side supports 204 and 206. Each wing part 200 and 202 and each side support 204 and 206 is designed to slide along an inner surface 210 of hollow elongated tube member 70 thereby providing stability and support for hub element 120 and medical needle apparatus 100. On a proximal end 212, hub element 120 comprises a releasible (e.g. threaded) connector 216 for a secure, but releasible attachment to puller 90. On a distal end 218, hub element 120 comprises a tube gripping hub member 220 for attachment to elastic tube 180. While it may be necessary for some materials used in fabrication of tube 180 to use an adhesive for attachment to hub member 220, adequate attachment has been achieved by physically stretching tube 180 over a slightly larger hub member 220.

Figure 6:
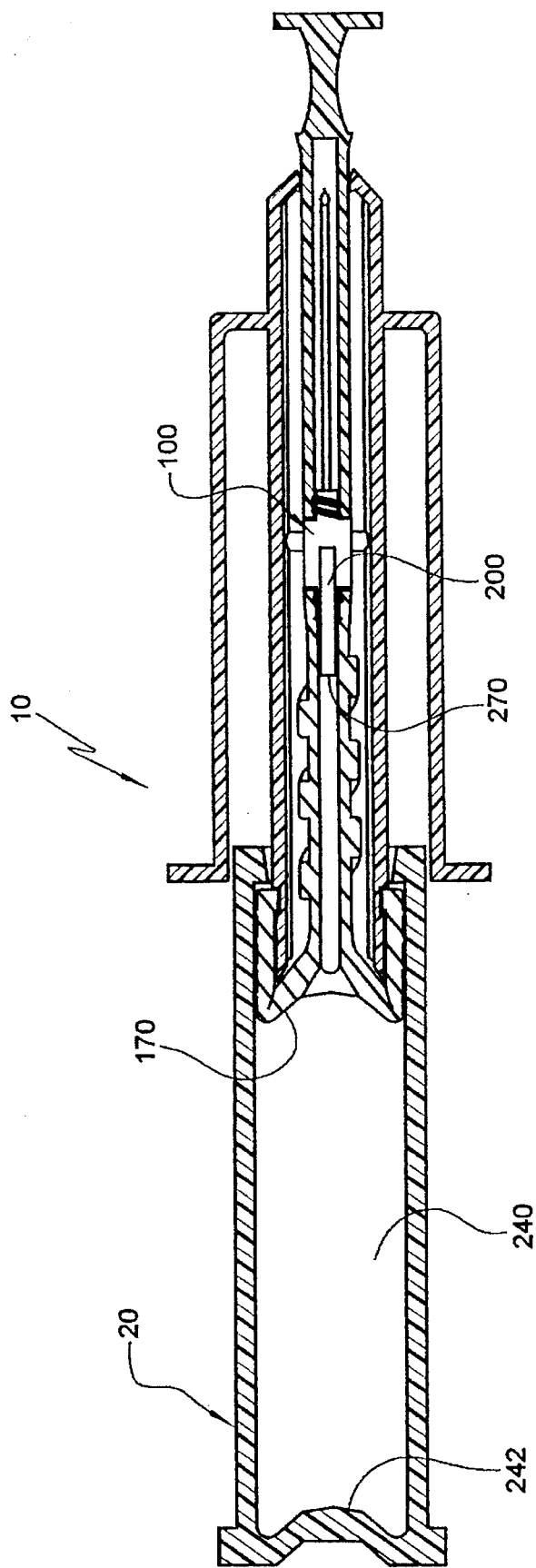
FIG. 6 is a cross section of the combination in an axial orientation as seen in FIG. 3, but with a barrel section extended outward from a plunger section.
Figures 7, 7A:
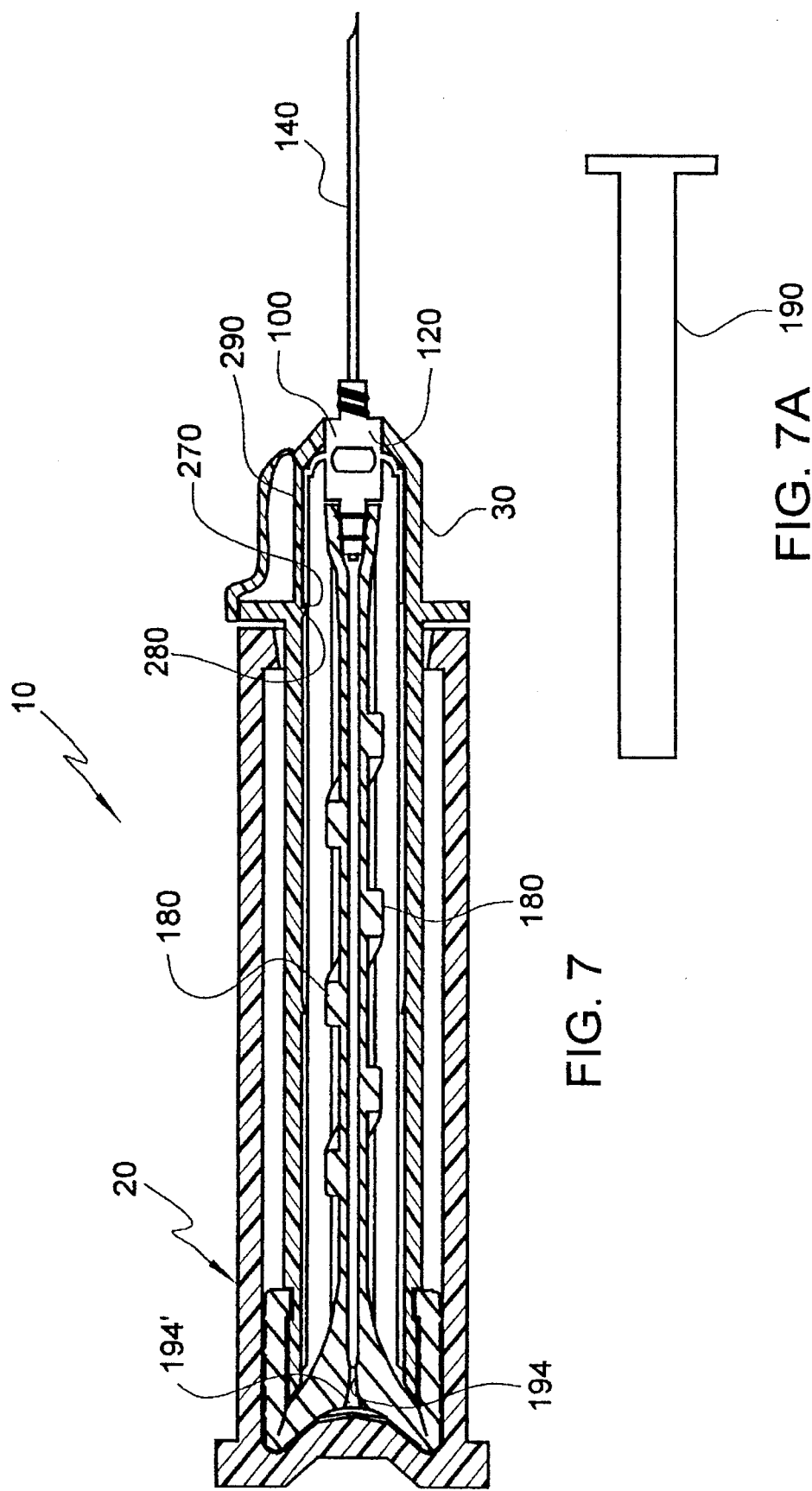
FIG. 7 is a cross section of a lateral elevation of the combination in the orientation seen in FIG. 2, but with the medical needle apparatus extended to dispose the needle for use and with a needle cover removed.
FIG. 7A is a lateral elevation of the needle cover removed from the combination seen in FIG. 7.

Reference is now Made to FIGS. 5, 6 and 7 wherein apparatus and methods for extending medical needle apparatus 100 to a position where needle 140 is disposed for use and whereby valve 160 is opened to permit flow of fluid therethrough are seen. In FIG. 7, medical needle apparatus 100, in this case with medical needle 140 securely attached to hub element 120, is extended disposing needle 140 in position for use in a medical procedure. Needle cover 190 by which medical needle apparatus 100 was extended and thereafter removed is seen in FIG. 7A. Elastic tube 180 is stretched as apparatus 100 is extended to store retraction energy to return needle 140 to protective cover at the end of the medical procedure.

The stretching of tube 180 not only provides a flow path for fluid to and from needle 180 and stores retractive force for apparatus 100, but also opens normally closed valve 160. As seen in FIG. 4, tube 180 comprises linkages 222 and 224 which are integrally attached to slit valve 160. Thickness of linkages 220 and 224 depends upon the size of the inside diameter of tube 140 and length and thickness of the face 194 (and opposing face 194') of slit valve 160. Such thickness can be determined without undue experimentation. As seen in FIG. 5, stretching tube 180 decreases the diameter of tube 180 and distorts slit valve 160 to part opposing faces 194 and 194', thereby opening valve 160. While there are other devices and methods for accomplishing opening a normally closed valve as tube 180 is stretched, this particular embodiment is preferred because the valve 160 and tube 180 are made as a single part.

In some cases, it may be desirable to select a medical needle determined by situation and procedure rather than have a needle delivered as a predetermined element of a syringe. For this purpose, rather than providing a needle cover 190, a puller 190' having a hub apparatus attachment such as that seen as an example in FIG. 8 can be used. Note that a medical needle apparatus 100' comprising a hub element 120' is used rather than medical needle apparatus 100 and associated hub element 120. The major difference is in the hub elements and particularly in the connection to pullers used. In the case of the embodiment of FIG. 8, puller 190' comprises a female luer-lock fitting 230 and hub element 120' comprises a complementary male luer-lock fitting 232. Note that use of luer fittings provides an excellent seal to close any pathway into hub element 120' as well as providing a compatible connector for affixing a medical needle to hub element 120' after medical needle apparatus 100' has been extended for use.

Generally, device 10 can be used as either a standard syringe or a pre-filled syringe. If device 10 is simply used as a standard syringe, there is no need to provide access for filling the syringe other than through a medical needle. Also, in this case, there may be no need to provide a normally closed valve, such as valve 160. In either case, barrel 20 and interfacing surface 170 combine to define a space 240 wherein medical or biological fluid resides either prior to or after a medical procedure.

Though not absolutely necessary, it is preferred that barrel 20 at end 50 comprise a generally frustoconical inner surface 242 and that interfacing surface 170, juxtaposing inner surface 242, have a complementary shape to facilitate expulsion of gas from space 240. In the case of the simple syringe application, surface 242 is formed as a continuous, integral element formed as a part of barrel 20.

Figure 9:
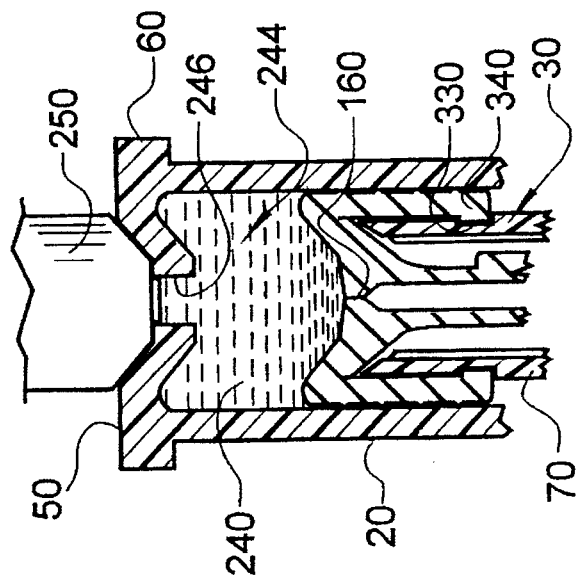
FIG. 9 is a segment of a cross section of a vertically oriented syringe/medical needle apparatus combination having a filler orifice disposed beneath a filler nozzle for the purpose of prefilling the syringe with a medical fluid.
Figure 10:
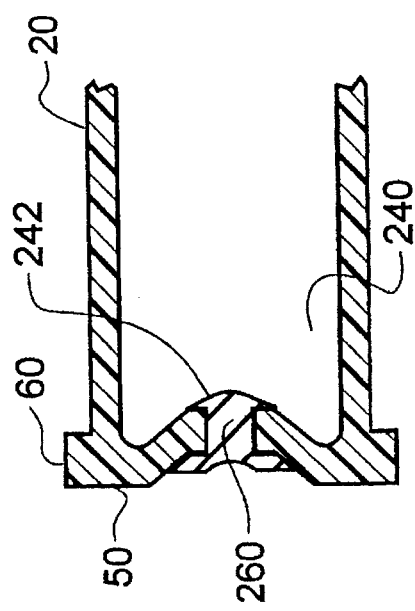
FIG. 10 is a horizontally oriented segment of a cross section of the syringe/medical needle apparatus combination seen in FIG. 9 with a plug placed in the filler orifice.
Figure 8:
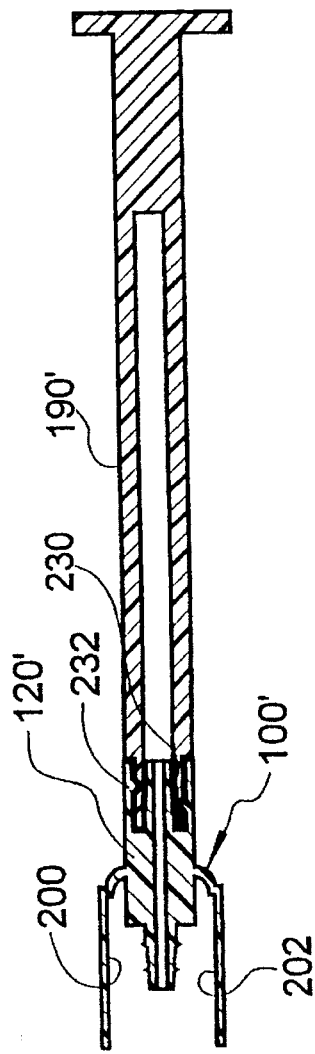
FIG. 8 is a cross section of a hub part of a medical needle apparatus connected via a luer-lock fitting to a part used as a puller to extend the medical needle apparatus.

To augment filling space 240 with a medical fluid, such as liquid 244 in FIG. 9, an orifice is provided, such as orifice 246 seen in FIGS. 9 and 10. A preferred method for pre-filling device 10 is to orient device 10 vertically with the proximal portion downwardly disposed. A pliant nozzle, such as nozzle 250 in FIG. 9, is sealably disposed against end 50 and orifice 246. While surface 170 is in contact with surface 242, a connection to a vacuum is made through nozzle 250 to evacuate gas from space 240. Thereafter, a connection is made with a vessel containing the liquid to be stored in device 10 through a low resistance pathway via nozzle 250 and plunger part 30 is moved downward to draw liquid 244 into space 240. Note that, other than access through orifice 246, there is no escape path for liquid form device 10 until valve 160 is opened. Also note that a secondary seal can be provided, such as by luer-lock fittings 230 and 232, to prevent evaporitive escape of liquid.

Once space 240 is filled with a predetermined volume of liquid 244, a plug (such as plug 260 seen in FIG. 10) is used to seal orifice 246 from further liquid flow. As one who is skilled in the art of filling and sealing medical vials would understand, this method of filling and sealing is only one of many methods available in the art. Other such methods may be used within the scope of this invention to safely and effectively fill and ready device 10 for use as a pre-filled syringe.

With the exception, of medical needle apparatus 100 and 100' extension and retraction, device 10 is generally used as a standard medical syringe is used, requiring but a minimum of training. Generally, puller 90 is drawn outward from plunder part 30 to extend medical needle apparatus 100 or 100' for use. As seen in particular in FIG. 7 (but also in FIGS. 2, 3, 6, 11, 12 and 13) hub element 120 (and 120') comprises a wing part 200 which extends outward toward inner surface 210. Preferably wing part 200 is slightly compressed inside plunger part 30 to retain a moderate outward pressure against surface 210.

Wing part 200 comprises a distal blunt end 270 special formed to provide a latching contact. When medical needle apparatus 100 (or 100') is drawn outward from plunger 30 to a position where medical needle 140 is made ready for use, end 270 is brought into latching contact with a protrusion 280 on inner surface 210, protrUsion 280 acts as a catch for end 270.

It should be noted that in an area of plunger part 30 immediately proximal to protrusion 280 is a thinned depressible section 290. Section 290 is sufficiently thinned to be facilely depressed in a manner and with forces consistent with depressing a key on a membrane keyboard. By such depression wing part 200 end 270 (acting as a latch) is released from protrusion 280 (a catch). Energy stored in extended tube 180 automatically causes retraction of medical needle apparatus 100 (or 100') to withdraw medical needle 140 inside hollow tube member 70. Such a retracted needle 140 is seen in FIGS. 12 and 13.

Dangerous needlestick problems related to recovering bared medical needles have resulted in rules being made and enforced which ban recovering medical needles unless special conditions or equipment make such recovering safe, both for the care giver and the patient. However, there are many reasons why it would be desirable to recover a medical needle so that it can be used a plurality of times. Such reasons include, the double use of a medical needle to pre-fill a syringe through the medical needle at a site remote from the patient and transport the filled syringe for delivery to the patient and delivering medication from the same syringe to the same patient following a procedure comprising incremental steps.

In each of the above cases, the medical needle should be recovered in the interim before a subsequent use. For greatest safety, the medical needle should be retracted into a safe housing, such as into the hollow of plunger 30 immediately after each use and, in fact, directly from the patient, as is possible with this novel invention. For maximum safety, a medical needle should be only uncovered immediately prior to use and immediately sheathed thereafter.

To provide for safely baring and recovering the needle, a retracted needle is recovered by the following inventive method using device 10. Note in FIG. 12 that medical needle 140 and hub element 120 are retracted to return needle 140 to a safely sheathed condition. As seen in FIG. 12A, elongated tube member 70 of plunger 30 comprises a plurality of inwardly disposed ribs 292, 294, 296 and 298. Outwardly extending parts of hub element 120, wing parts 200 and 202 and side supports 204 and 206 are constrained from axial displacement by ribs 292, 294, 296 and 298.

Note that wing part 200 is constrained by ribs 292 and 298, wing part 202 by ribs 294 and 296, side support 204 by ribs 298 and 296 and side support 206 by ribs 292 and 294. Note further that inward displacements of ribs 292, 294, 296 and 298 are disposed to centrally constrain, but allow linear displacement of hub element 120 and needle cover 190. Further, wing parts 202 and 204 and side supports 204 and 206 combine to restrain needle 140 in substantial coaxial direction relative to the long axis of tube member 70.

When needle 140, wing parts 202 and 204 and side supports 204 and 206 are so constrained, needle cover 190 can be safely and effectively re-inserted through orifice 86, rotated to teengage connector 216 and thereby be repositioned for reextending needle 140 for subsequent use. Note that both necessary conditions for safely and effectively recovering needle 140 with needle cover 190 are met as, first, the needle is safely sheathed while the recovering act is performed and, second, cover 190 is biased away from contact with needle 140 to protect sterility of needle 140 during the recovery process.

Of course, parts of needle cover 190 which may come in contact with needle 140 when cover 190 is removed after extending needle 140, must be designed to remain uncontaminated while cover 190 is removed and separate. As one who is skilled in the art of handling needle covers well understands, there are procedures currently known in the art for handling and protecting removed needle covers in such circumstances.

As is well known in the art of using and disposing of medical needles, it is often desirable to remove the option of further use of a medical needle after a medical procedure is completed. In those cases where needles are added to a syringe prior to retraction, a needle cover 190 or puller 190' cannot be reconnected to a hub element. In that case, the needle is safely retained and cannot be reused. However, in the case of a syringe designed for needle reuse as disclosed above, another element must be added to eradicate options for reuse.

Three different embodiments which can be used for destroying subsequent operability of device 10 are disclosed hereafter. First, attention is drawn to FIG. 14, in which only parts necessary to describe a way of permanently locking needle cover 190 into tube member 70 are seen. As seen in FIG. 14, nose cone 82 comprises an inwardly disposed annular shoulder 300, the surface of which is transverse to the long axis of needle 140 and tube member 70. As disclosed above, travel of needle cover 190 is constrained to be along the long axis of needle 140. Needle cover 190 comprises a raised shoulder 302 which incorporates a proximally disposed transverse face 304. As tube 180 will buckle when forced compressively and material of nose cone 82 will give sufficiently when needle cover 190 is forcibly pushed into tube member 70, such inward movement ultimately causes shoulder 300 to lock against face 304 sealing device 10 against further use.

Elements used in a second method of eradicating the possibility of further use after completion of medical procedure are seen in FIG. 2. Note that proximally disposed sections of wing parts 200 and 202 each comprise a transversely disposed latching segment 310 and 312, respectively. Complementary catches 314 and 316 are disposed upon the inner surface 210 of tube member 70. These catches and latches are so placed that forcing needle cover 190 inward into tube member 70 with sufficient force and displacement to cause catches 314 and 316 to catch latches 310 and 312, respectively, securely constrains needle 140 inside tube member 70, thereby negating further use.

A plug 320, added to shield 84 (to form shield 84'), is seen in FIGS. 12 and 13 to provide a third method for sealing device 10 against further use. As seen in FIG. 12, shield 84' comprises plug 320 vertical and exteriorly disposed such that, after needle 140 is finally retracted, by lifting shield 84' for access to section 290 to cause the retraction, plug 320 is rotated approximately 90° and forced into tube member 70. Plug 320 comprises complementary surfaces to a catching surface, such as shoulder 300 to securely affix plug 320 to close device 10 against further use.

Of particular importance is the use of device 10 as a pre-filled syringe. Note that sealed parts must be tightly closed to maintain effectiveness of medical fluids contained within space 240. (See FIG. 9.) Plug 260, sliding seal 150, valve 160 and cover 190 and puller 190' connections to medical needle apparatus 100 should all provide a substantially closed environment for the medical fluid contained in the pre-filled syringe. Only when medical needle apparatus 100 is extended for use should valve 160 open. It is also preferred that only when puller 190' or cover 190 is removed is the medical fluid truly exposed to an external environment.

And so to ready device 10 for use, medical apparatus 100 is extended by pulling either cover 190 or puller 190' until latch 270 is caught by catch 280. Valve 160 is opened thereby. Either cover 190 or puller 190' is then removed. If puller 190' is used, a medical needle having a luer fitting is connected to medical needle apparatus 100.

As is common practice in medical injections, all gas is purged from the fluid pathway by vertically disposing device 10, with the medical needle 140 pointed upward, and decreasing volume 244 until the medical fluid is seen to escape needle 140. A predetermined volume, not necessarily all of the volume left in space 240, is dispensed. Upon completion of this segment of the procedure, medical needle 140 is retracted by depressing section 290.

As disclosed above, needle cover 190, having been protected from unacceptable contamination, can be reinserted and reconnected to recover medical needle apparatus 100 for subsequent use of the pre-filled syringe. Once needle 140 is recovered and the steps of extending and using device 10 in a continuing medical procedure are performed. Upon a final step of using device 10, cover 190 is forcibly inserted into tube member 70 to secure needle 140 from further use. As an alternative, plug 320 is securely affixed into orifice 86.

Figure 11:
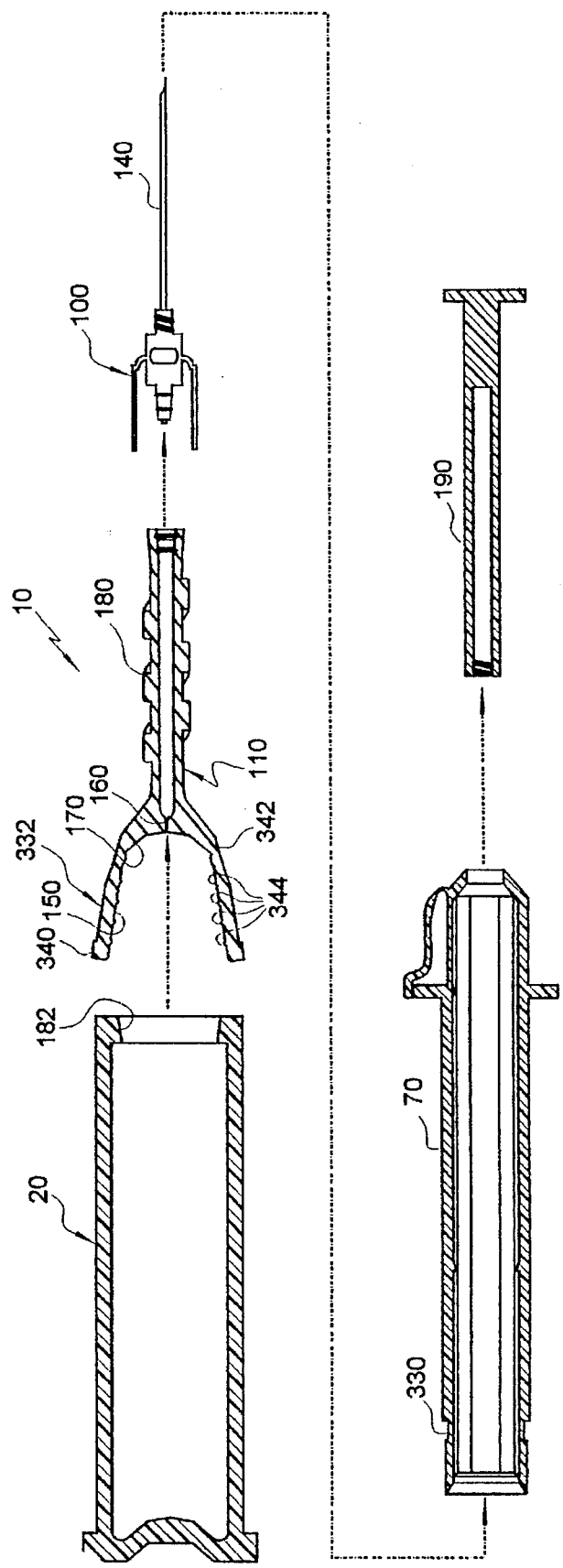
FIG. 11 is an exploded view of the combination seen in FIG. 1 with only the assembly step of attaching a medical needle to a hub completed.

Referring now to FIG. 11, device 10 assembly steps (of course all manufacture and assembly should be performed under appropriately clean conditions) are seen to comprise:

1. Fabrication by injection molding or other high volume, low cost process hub element 120 (or 120'). It is preferred to make medical hub element 120 from a synthetic resinous material which has sufficient flexibility and strength that extend parts (200 and 202) can be used as depressible latches. While no part of hub element 120 must contact the medical fluid, it is preferred that the selected material be inert both to bodily fluids and medically injectable fluids. Such material may be selected from an appropriate grade of polyurethane, polypropylene and polyethylene.

2. Medical grade steel, such as the steel currently used in disposable medical needles should be used for needle 140. In the case that medical needle 140 is provided as an integral part of hub element 120, needle 140 is preferably securely affixed to hub member 220 by adhesive processes currently well known in the art of medical needle fabrication. In the case where the medical needle is attached after extension of apparatus 100, hub element 120' comprises a luer-lock fitting to be connected initially to puller 190'.

3. The functions of component 110 may be performed by a plurality of parts. Note that when component 110 is made as a single, generally cylindrical, integral part it comprises seal 150, normally closed valve 160, interfacing surface 170 to a ventral surface of a posterior portion of barrel 20 and an elastic tube 180. Starting from a proximal end elastic tube 180 is normally closed (unless tube 180 is stretched) by valve 160. Valve 160 opens on a distal side to interfacing surface 170 which extends distally to form seal 150. Operation of seal 150 as a fluid control device has been disclosed above and will not be repeated here. Tube 180 also functions as a regurgitant fluid control device using processes disclosed in detail hereafter. Component 110 may be made from a plurality of currently available products such as medical grade latex and silicone rubber. However new and better products are continuously being introduced into the marketplace. Important elements which should be considered when selecting a new material comprise knowledge that the material is effectively inert to both bodily fluids which might contact it, that it may be extended to a length which permits latching apparatus 100 in a forward condition and at which length it will retract an inserted needle 140 and it will form an effective seal both for seal 150 and valve 160. Component 110 is affixed directly to hub element 120 (or 120') via hub member 220.

4. The joined combination of apparatus 100 and component 110 is then inserted into the hollow of tube member 70, with wing parts and side supports of apparatus 100 disposed as described heretofore. As seen in FIG. 11, tube member 70 comprises an annular groove 330 and a section 332 of component 110 comprising seal 150 comprises an annular ridge member 340 (an integral o-ring) which is complementary to groove 330. Also section 332 comprises a thinned, foldable annular region 342 which permits section 332 to be folded to double about the exterior surface of tube member 70 whereby component 110 is securely affixed about tube member 70 with member 340 residing in groove 330 to form seal 150 thereupon. Note that component 110 comprises a series of annular rings 344 to enhance performance of seal 150.

5. Once component 110 is affixed to tube member 70, needle cover 190 (or puller 190') is affixed to hub element 120 (or 120').

6. Finally, seal 150 portion of component 110 and tube member 70 is forced through opening 64 to complete assembly of device 10. Note that barrel 20 is shown in FIG. 11 as a barrel having a closed distal end. Of course barrel 20 can also have an open, but closable distal end, as earlier disclosed. Though other materials may be used, Needle cover 190 (puller 190') is preferably made from medical grade polypropylene. Similarly plunger 30 is preferably made from medical grade polypropylene, although other materials which have similar depressible qualities of thin members may also be used within the scope of the invention. As seen in FIG. 14, plunger 30 may be made from two separately injection molded parts and then joined later. Ultrasonic bonding is preferred. Selection of materials for barrel 20 is highly dependent upon fluids stored therein in the pre-filled application. Materials may range from synthetic resinous materials to medical grade glass. If a material which is not absolutely shatterproof is not used, at least a protective cover should be placed over section 60 at distal end 50. (Not shown.)

7. In a fully assembled device, it is preferable to physically secure cover 190 (or puller 190') to nose cone 82 by heat staking or the like to provide a sterility barrier.

Figure 15:
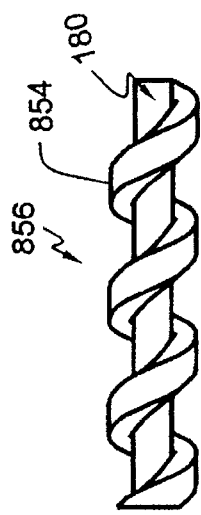
FIG. 15 is a perspective of an elastic tube with a helical member wrapped about the tube.
Figure 16:
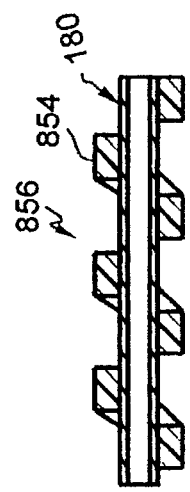
FIG. 16 is a cross section of the elastic tube and helical member seen in FIG. 15.
Figure 17:
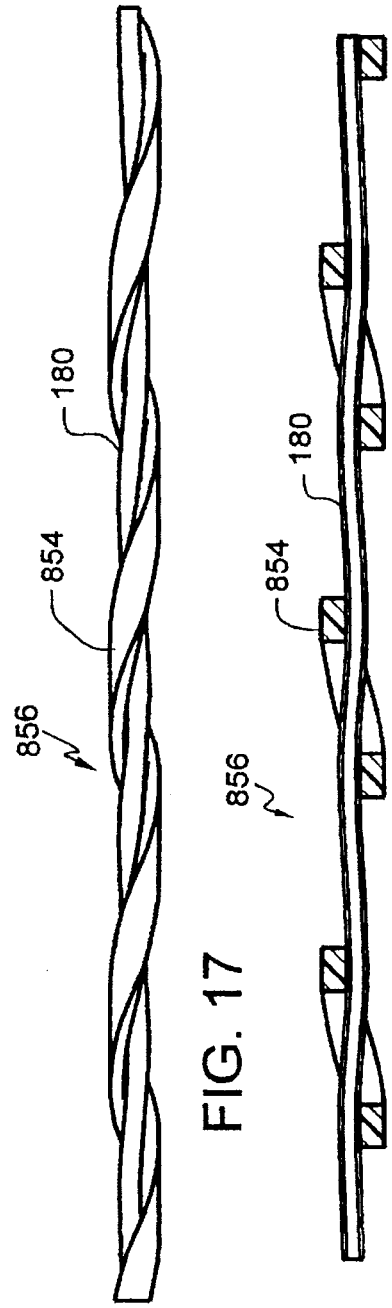
FIG. 17 is a perspective of the elastic tube of FIG. 15 stretched and the helical member also elongated to close tightly about the elastic tube to distort the tube from a round geometry.
Figure 18:
FIG. 18 is a cross section of the elastic tube of FIG. 17.

A method for retricting the volume of a stretched tube to be less than the volume of tube 180 in a relaxed state is seen in FIGS. 15–18. FIGS. 15 and 16 show tube 180 in a relaxed state. FIGS. 17 and 18 show the tube 180 in a stretched state. In simplest terms, tube 180 is seen to be disposed within a helical wrap 854 to form a combination 856. As is well known in the art, if wrap 854 is relatively inelastic, extending wrap 854 to nearly its resting length will cause wrap 854 to approximate a nearly straight line. As the cross sectional area of an elastic tube decreases by approximately the power of the number of rest lengths the tube is stretched, one who is skilled in the art of helix formation and elastic tube dynamics understands that there exists a critical pitch of the helix beyond which the internal volume of the helix decreases more rapidly upon extension than the internal volume of an interposed tube, such as tube 180.

Calculation of the critical pitch is relatively straight forward, as the following example shows. The general cartesian coordinate equations for a helix are:

$$x = a \cos \theta = a \cos ns \qquad \text{Eq. 1}$$

$$y = a \sin \theta = a \sin ns \qquad \text{Eq. 2}$$

$$z = 1 \qquad \text{Eq. 3}$$

where:

a is the radius of the helix.

$\theta$ is the angle of rotation of the helix about its long axis.

s is the distance along the helix.

l is the distance along the long (z) axis of the helix.

n is the angular rate of change of $\theta$ as a function of l.

An equation for the length of a segment along the helix is given by:

$$ds = sqrt(dx^2 + dy^2 + dz^2) \qquad \text{Eq. 4}$$

Differentiating Eq.'s 1, 2 and 3, with respect to s and l, and substituting into Eq. 4:

$$ds = sqrt(a^2 n^2 \sin^2 ns \, ds^2 + a^2 n^2 \cos^2 ns \, ds^2 + dl^2) \qquad \text{Eq. 5}$$

Which reduces to:

$$ds = sqrt(a^2 n^2 ds^2 + dl^2) \qquad \text{Eq. 6}$$

or:

$$ds^2(1 - a^2 n^2) = dl^2$$

Integrating over the length (S) of the helix and of a distance (L) to which the helix is spread, the relationship between a and n is given by:

$$S = L/sqrt(1 - a^2 n^2) \qquad \text{Eq. 7}$$

The value of n may be given as:

$$n = 2 \pi N/S \qquad \text{Eq. 8}$$

Where N is the total number of turns in helix length S.

Substituting for n and squaring both sides of the equation and solving for radius a:

$$S = L/sqrt(1 - a^2 [2 \pi N/S]^2) \qquad \text{Eq. 9}$$

or:

$$S^2 = S^2 L^2 / (S^2 - a^2 [2 \pi N]^2) \qquad \text{Eq. 10}$$

which yields:

$$L^2 = (S^2 - a^2 [2 \pi N]^2) \qquad \text{Eq. 11}$$

Solving for a:

$$a = Sqrt(S^2 - L^2)/2 \pi N \qquad \text{Eq. 12}$$

Solving for N:

$$N = Sqrt(S^2 - L^2)/2 \pi a \qquad \text{Eq. 13}$$

Through experimentation, it has been found that change in internal volume of a stretched tube between two known points along a length of the tube (not comprising endpoints where the tube is connected to a hub or the like) is not changed substantially by stretching.

Therefore, the following relationships apply:

$$V = 2\pi a^2 l' \qquad \text{Eq. 14}$$

where:

l' is also the length of the section between the two known points.

Note that, since V is a constant:

a is substantially equivalent to sqrt(K/l') where K is an easily derived constant.

It has also been determined experimentally that the total internal volume (V') of an elastic tube does vary due at least to volumetric variations at tube ends where unions are made with connecting hubs. This variation generally causes the volume of a stretched tube to be greater than the volume of the same unstretched tube. This change in volume results in fluid regurgitation when the tube is used as a retracting mechanism and concurrently as a container and transport path for fluid received from a medical needle. It is for this reason that use of a helix wrap (such as wrap 854) is preferably used to reduce or restrict an increase in volume of the stretched tube.

An example of a method of design and employment of a volume restricting helix is given below:

Using a plastic tube in place of the medical needle to permit visual observation of the increase in volume due to stretching an elastic tube to a length three times its rest state length, the increase (δV') in volume was observed to be:

δV'=6.5 microliters (μl)

in an elastic tube having the following rest state dimensions:

O.D.$_{at\ rest}$=3.18 mm

I.D.$_{at\ rest}$=1.59 mm

Length$_{at\ rest}$=19.1 mm

Internal Volume$_{at\ rest}$=38 μl and having the following stretched dimensions:

Nominal O.D.$_{stretched}$=1.83 mm

Calculated I.D.$_{stretched}$=0.92 mm

Length$_{stretched}$=57.2 mm

Internal Volume$_{stretched}$=45 μl

Nominal tube O.D. volume$_{stretched}$=150 μl

Assuming that a compressive reduction in total tube volume (including the tube itself) would result in a reduction in internal volume of substantially the same amount, a reduction of the O.D. volume to approximately 143 μl when the tube is stretched requires compressing the exterior of the tube to an equivalent average diameter of about 1.78 mm.

Because the number of turns of the helix is not permitted to change when the helix is lengthened from a rest state to a stretched state of tube 180 in this application, Eq. 13 (reproduced below) can be used to evaluate the length S and number of turns N of the helix.

$$N = Sqrt(S^2 - L^2)/2\pi a \qquad \text{Eq. 13}$$

By entering values for the rest or unstretched state (r), Eq. 13 becomes:

$$N = Sqrt(S^2 - L_r^2)/2\pi a_r \qquad \text{Eq. 13r}$$

Likewise, entering values for stretched state (s), Eq. 13 becomes:

$$N = Sqrt(S^2 - L_s^2)/2\pi a_s \qquad \text{Eq. 13}$$

and:

$$Sqrt(S^2 - L_r^2)/2\pi a_r = Sqrt(S^2 - L_s^2)/2\pi a_s$$

squaring and cross multiplying:

$$(S^2 - L_r^2)(2\pi a_s)^2 = (S^2 - L_s^2)(2\pi a_r)^2$$

solving for S:

$$S^2 = (L_r^2 a_s^2 - L_s^2 a_r^2)/(a_s^2 - a_r^2)$$

For the example given above:

S=68 mm

Evaluating N (number of turns) from equation 14s:

N=6.6 turns

However, as seen in FIGS. 17 and 18, wrap 854 does not fully enclose tube 180 and, therefore, tube 180 is periodically free to expand outward from constraint of wrap 854 in the gaps between constraint of the helix. For this reason, the number of actual turns ($N_a$) should be fewer than the predicted value of N, above. Even so, a more desirable value of $N_a$ can be arrived at without undue experimentation by one skilled in the art of fluid dynamics. It is well known in elastic tube extrusion art to enclose one or more helically wound coils of support material in the wall of extruded tubes. Such enclosed coils are most often used to add strength to the tube to support the tube against inadvertent collapse or to be able to withstand high pressure. A process similar to such an extrusion process can be used to make combination 856 by properly controlling pitch and using the coil not to support the tube against collapse, but to constrict the tube when it is stretched with a predetermined pitch of the helix.

The inventions disclosed herein may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A combination comprising a medical syringe and an extendable and self-retracting medical needle apparatus, said combination comprising:

a syringe barrel part comprising an elongated,. hollow cylindrical portion, having an internal surface, and an end closing portion also having an internal surface;

a plunger assembly at least partially disposed within the hollow cylindrical portion and, in combination with said barrel part forming a fluid containment space, the volume of which is varied by repositioning the barrel part relative to the plunger assembly, the space being at least partially constrained by said internal surfaces, said plunger assembly comprising:

an elongated hollow housing having an outside surface which is sized to slide within, but not in contact with, said cylindrical internal surface and having a first end disposed within said barrel and a second end associated with extension of said apparatus said housing further comprising a depressible portion which is accessible to a user outside said barrel part;

a slidable seal disposed between said internal surface of said cylindrical portion and said outside surface to form a fluid seal therebetween;

a catch for a latch, said catch being disposed to lodge the latch in physical communication with the depressible portion when the apparatus is extended;

the self-retracting medical needle apparatus comprising:

an elastic tube connected at a posterior end to said housing at the first end and, at least when the apparatus is extended, providing a stored retractive force and a fluid communicating pathway between a medical needle and the fluid containment space when the apparatus is ready for use;

hub means comprising a posterior tube connection by which the apparatus is securely affixed to an anterior end of said elastic tube, a releasible union by which said apparatus is attached to a pull mechanism and, thereby, extended for use from a transport position within said housing to a position at which a medical needle is disposed for use in a medical procedure and the latch for the catch, said latch being releasible from said catch by depressing said depressible portion by an action transverse to the long axis of the needle thereby retracting the medical needle independent of position of the barrel part relative to the plunger assembly.

2. The combination according to claim 1 further comprising a normally closed valve disposed between the space and the fluid communicating pathway to form a closed space for containment of biological fluids, said valve being opened when the apparatus is extended.

3. A combination according to claim 2 wherein said normally closed valve is a slit valve.

4. A combination according to claim 3 wherein the slit valve and elastic tube are formed as a single part.

5. A combination according to claim 3 wherein the slit valve, the elastic tube and the slidable seal are formed as a single part.

6. A combination according to claim 2 wherein said end closing portion comprises an opening wherethrough said closed space is filled with liquid.

7. The combination according to claim 6 further comprising a stopper which is formed to be secured in said opening thereby assure containment of the liquid until released via opening of said normally closed valve.

8. The combination according to claim 1 further comprising tube constricting means which squeeze the tube when extended such that the space and tube, in combination, comprise a smaller fluid containing volume when the tube is extended than when the tube is retracted.

9. A combination according to claim 8 wherein the tube and tube constricting means are formed as a single part.

10. A combination according to claim 8 wherein the tube, normally closed valve, and tube constricting means are made as a single part.

11. A combination according to claim 8 wherein the slidable seal and tube constricting means are made as a single part.

12. A combination according to claim 8 wherein the slidable seal, normally closed valve, tube constricting means and tube are formed as a single part.

13. The combination according to claim 1 further comprising a mechanically removable protective shield which protects the depressible portion from inadvertent distortion until removed.

14. A combination according to claim 1 further comprising a medical needle securely affixed to said hub means.

15. A combination according to claim 1 wherein said hub means comprises a luer-lock fitting whereby a medical needle is affixed after said hub means are extended.

16. The combination according to claim 1 further comprising a puller which is securely but removably affixed to the hub means and which is used to extend the hub means to a position where the needle is used in a medical procedure.

17. A combination according to claim 16 wherein the hub means comprise securely affixed medical needle and the puller is a cover which protects the medical needle during transport and prior to removal providing access to the medical needle for a medical procedure.

18. A combination according to claim 17 wherein said housing comprises guides which, after a needle has been retracted into said housing, permit a cover to be safely guided to recover the needle without further contamination of said needle to permit said cover to be safely and effectively reattached to said hub means and subsequently be used to reextend said needle for a subsequent use.

19. A combination according to claim 17 wherein said housing comprises at least one other catch and said cover comprises at least one complementary latch which are used to securely capture said cover and preclude succeeding use of said combination when the cover is forced into the housing with sufficient force to buckle the elastic tube and to a position where the latch is seized by the catch.

20. A combination according to claim 1 wherein said housing comprises handle means which permit single handed manipulation of the barrel and housing for the purpose of causing transfer of fluid through the pathway.

21. A combination according to claim 1 wherein said space comprises a medical liquid, prefilled into said combination for transport to a site of a medical procedure for direct and immediate delivery of the medical liquid during a medical procedure.

22. The combination according to claim 1 wherein the internal surface of the end closing portion is convex in shape having a centrally disposed apex.

23. The combination according to claim 22 wherein said apex is juxtaposed said pathway.

24. The combination according to claim 23 wherein said housing, said slidable seal and said elastic tube, in combination comprise a surface which is juxtaposed said internal surface of the end closing portion and which is complementary to the shape of that internal surface such that gas contained within the space is facilely purged by vertically orienting said combination with the needle pointed upward in a manner well understood and practiced in the art of medical syringe use.

25. The combination according to claim 1 wherein the hub means comprises a hub latch and the housing comprises a hub catch disposed to securely capture and seize said hub latch when the puller is forced into the barrel with sufficient force to buckle the tube.

26. The combination according to claim 1 further comprising a mechanically removable protective shield which protects the depressible portion from inadvertent distortion until removed and which comprises a plug which is securely affixed to said housing to preclude any further use of the combination after retraction of the medical needle.

27. A method for using a pre-filled syringe comprising the following steps:

(a) providing a pre-filled syringe comprising a closed cavity which is filled with a medical fluid, an extendable and retractable medical needle means initially safely disposed in a protective housing, a normally closed valve which maintains said cavity in a closed and sealed state until the medical needle means is extended and a puller used to extend the medical needle means for use;

(b) using the puller, extending the medical needle means for use, thereby opening said valve;

(c) removing the puller from the medical needle means;

(d) purging gas from the syringe through said medical needle means;

(e) dispensing at least a portion of the medical fluid;

(f) fully retracting the medical needle means back into the housing by action of depressing a depressible portion of said housing.

28. The method according to claim 27 wherein step (a) further comprises providing a medical needle securely affixed to said medical needle means and said puller is a needle cover and step (b) comprises using the cover as the puller and thereby extending a medical needle for use.

29. The method according to claim 28 further comprising the following steps:

(g) reinserting the needle cover into the housing and thereby safely and effectively recovering the retracted medical needle and reattaching said needle cover to the medical needle means;

(h) repeating steps (b) through (f).

30. The method according to claim 29 comprising a further step of forcing the needle cover into the housing until the cover is firmly and securely seized to negate subsequent use of the pre-filled syringe.

31. The method according to claim 27 wherein step (c) comprises securely attaching a medical needle to be used with said pre-filled syringe after removal of said puller.

* * * * *